United States Patent [19]
Rudolph et al.

[11] Patent Number: 4,933,434
[45] Date of Patent: Jun. 12, 1990

[54] PROCESS FOR OBTAINING RENATURED PROTEINS

[75] Inventors: Rainer Rudolph, Regensburg; Stephan Fischer, Weilheim, both of Fed. Rep. of Germany

[73] Assignee: Boehringer Mannheim GmbH, Mannheim, Fed. Rep. of Germany

[21] Appl. No.: 298,274

[22] Filed: Jan. 13, 1989

Related U.S. Application Data

[63] Continuation of Ser. No. 30,455, Mar. 25, 1987, abandoned.

[30] Foreign Application Priority Data

Apr. 8, 1986 [DE] Fed. Rep. of Germany ....... 3611817

[51] Int. Cl.$^5$ ................................................. C07K 3/08
[52] U.S. Cl. .................................... 530/405; 530/402; 530/404; 530/406; 530/408; 530/409; 530/410; 530/412; 530/418; 530/422
[58] Field of Search ............... 530/412, 418, 422, 402, 530/408, 409, 410, 404–406

[56] References Cited

U.S. PATENT DOCUMENTS

| | | | |
|---|---|---|---|
| 4,216,141 | 8/1980 | Rivier et al. | 530/333 |
| 4,530,787 | 7/1985 | Shaked et al. | |
| 4,656,255 | 4/1987 | Suly et al. | 530/417 |

FOREIGN PATENT DOCUMENTS

| | | | |
|---|---|---|---|
| 0114506 | 8/1984 | European Pat. Off. | 435/68 |
| 0208539 | 1/1987 | European Pat. Off. | 435/68 |
| 3329624 | 3/1984 | Fed. Rep. of Germany | |
| 8304418 | 12/1983 | United Kingdom | |
| 8605809 | 10/1986 | United Kingdom | 435/68 |

OTHER PUBLICATIONS

Marston, "Purification of Eukarytic Polypeptides Synthesized in *E. Coli*", Biochem J., 1986, 240, pp. 1–12.
Downstream Processes: Equipment and Technique, 1988, Alan R. Liss Inc., pp. 205–240.
Merge et al., "Purification of Proteins From Cell Culture Supernatants", *Develop Biol. Std.*, vol. 66, 1987, pp. 391–401.
Pharmacia Bulletin #50-01339, 1986, vol. 13(6), Separation New, "A Strategy for Protein Purification", pp. 2–7.
Orsini et al., *JBC*, 253, 1978, pp. 3453–3458.
Odorzynski et al., *JBC*, 254, 1979, pp. 4291–4295.
Smithies, *Science*, vol. 150, pp. 1595–1598.
Lehinger, "Principles of Biochem", 1982, pp. 177–179.
Jaenicke, Biophys Struct Mech 8: 231–256 (1982).

*Primary Examiner*—Garnette D. Draper
*Attorney, Agent, or Firm*—Felfe & Lynch

[57] ABSTRACT

The present invention provides a process for the renaturation of denatured proteins in solution in a renaturation buffer, wherein a solution is prepared of the protein to be renatured in the critical concentration in a selected buffer and, after formation of the folding intermediate, further protein to be renatured is added in the amount necessary for the achievement of the critical concentration.

6 Claims, 5 Drawing Sheets

PROCESS FOR OBTAINING RENATURED PROTEINS

This application is a continuation, of application Ser. No. 030,455, filed Mar. 25, 1987, now abandoned.

The present invention is concerned with a process for renaturing proteins.

By renaturation of proteins in the scope of the present invention is to be understood the production or reobtaining of the normal biological function of proteins, it thereby being understood that the natural secondary, tertiary and possibly quanternary structures are reobtained.

The problem of renaturing proteins is of great importance since biologically active proteins are frequently denatured by the treatments carried out upon them, for example in the case of the separation thereof from accompanying materials, and the interesting biological properties are hereby lost completely or partly. Renaturation is also of importance in the case of synthetic proteins and of proteins produced by gene technology since, in many cases, there is thereby obtained only the correct primary structure, i.e., the amino acid sequence, but the desired utilisation of the biological activity requires that a renaturation takes place with the formation of the natural secondary, tertiary and possibly also quaternary structure.

From U.S. Pat. No. 4,530,787, it is already known how to oxidize synthetic proteins, which contain reduced cysteine, with iodosobenzoate with the reobtaining of their biological activity. Even if this method were to be of general applicability, it would only solve a part of the problem of the renaturing of proteins.

G. Zettlmeissl, R. Rudolph and R. Jaenicke, Biochemistry, 18, 5567–5575/1979, have investigated the renaturation of an oligomeric enzyme, namely lactate dehydrogenase, with reobtaining of the tertiary structure thereof and have thereby ascertained that, in the case of such a renaturation, two competing reactions take place, namely, the renaturation on the one hand and the formation of inactive aggregates on the other hand. For the achievement of good yields of renaturation, care must thereby be taken that a limiting concentration of enzymes in the solution is not exceeded. However, a general process for the renaturing of proteins cannot be derived from this.

Therefore, it is an object of the present invention to provide a process which, in general, permits an improvement of the renaturation of proteins.

Thus, according to the present invention, there is provided a process for the renaturation of denatured proteins in solution in a renaturation buffer, wherein a solution is prepared of the protein to be renatured in the critical concentration in a selected buffer and, after formation of the folding intermediate, further protein to be renatured is added in the amount necessary for the achievement of the critical concentration.

The process is based upon the discovery that a highest possible yield of renatured protein can be achieved with a simultaneous maximum speed of renaturation when a definite critical concentration value of the denatured protein to be renatured in the solution is not exceeded, this value being dependent upon the nature of the protein in question and the conditions under which the renaturation is carried out. It is thereby important that the relationship of two reactions competing with one another, namely, the undesired formation of inactive protein (e.g. aggregates) on the one hand and the formation of a folding intermediate on the other hand, which subsequently passes over into the final native renatured protein, is so displaced that only the smallest possible proportion of inactive protein can arise. For this purpose, it is necessary to take into account the protein-specific and the condition-specific critical concentration of the protein to be renatured, the renaturation kinetics and the time up to the formation of the folding intermediate.

These three parameters which are important for the process can be readily determined. The critical concentration can be ascertained by means of a calibration curve which is obtained by using different concentrations of denatured protein in the particularly selected renaturing buffer and measuring the end yield of renatured protein achieved in a predetermined period of time. The critical concentration corresponds to the value at which the highest yield of native renatured protein is obtained.

The renaturing kinetics can also be determined according to known methods. There is thereby determined, at the maximum possible concentration, the time necessary for the conversion into renatured protein. The time up to the formation of the folding intermediate can finally be determined according to a whole series of different processes. A first method of determination consists in the measurement of the circular dichroism (CD). A wavelength is thereby preferably chosen at which a large signal is obtained and then the corresponding curve is measured, whereby, as a rule, a steep increase takes place in a relatively short period of time and the curve then flattens out as soon as the folding intermediate is formed. A further possibility consists in monitoring the disappearance of the SH groups by the formation of intramolecular disulphide bridges. However, it is thereby to be observed that no intermolecular disulphide bridges are to be formed, which can be determined by monitoring the molecular weight which, in the latter case, would increase.

A further possibility consists in fluorescence measurement. This is based upon the tryptophane or tyrosine fluorescence which changes when the aromatic side-chains are transferred to a hydrophobic region of the folded protein. Further possibilities are limited proteolysis since, with increasing formation of the folding intermediate, the proteolytic attack is also reduced. It is also possible to carry out this determination by hydrodynamic measurements. For example, there may be measured the intrinsic viscosity which decreases since the folding intermediate leads to the formation of a solution with lower viscosity.

In practice, it is sufficient to determine the critical concentration and the time up to the formation of the folding intermediate protected against the side reaction to inactive protein and, in each case, to commence with the critical concentration and, after formation of the folding intermediate, to replenish the denatured protein consumed in the meantime from the solution by conversion. This can take place stepwise in that the times and critical concentrations are predetermined and then, in each case, after formation of the intermediate, there is added the known amount of denatured protein. Alternatively, the process can also be carried out continuously in that there is newly added precisely just as much denatured protein as has disappeared by new formation of the folding intermediate. In this way, the renaturation can be carried out in a cyclic process in which, for example, the protein to be renatured is continuously added to the renaturation reactor either dissolved in a solvent appropriate therefor, for example highly diluted hydrochloric acid, or in lyophilised form. In each case the denatured protein is replenished in such an amount that the optimum renaturation concentration is obtained. The renaturation buffer is simultaneously added continuously in such a composition that the conditions remain constant with regard to pH value, substance concentrations and the like. By appropriate construction of the reactor, which can be, for example, in the form of a loop, and the flow rate defined by the rate of addition of protein and buffer solution, there can be defined a period of incubation which corresponds to the time up to the formation of the folded intermediate. Thereafter, reactivated protein is continuously removed, and the retentate optionally subjected to a separation into inactive aggregate and active protein. The continuous process is preferably carried out in such a manner that the regenerated buffer solution is again returned continuously to the reactor.

In the case of the continuous version of the process according to the present invention, it is preferred initially, as in the case of the non-continuous process, to add the denatured protein batchwise in the above-described way until an optimum concentration of renatured active protein has been obtained. As soon as this is achieved, continuous removal of the relatively concentrated solution of reactivated protein is commenced and only then is the actual continuous process commenced. The initial phase, in which the concentration of reactivated protein still increases, is, therefore, introduced before the actual continuous process. As optimum concentration of renatured protein, there is thereby to be understood the highest possible concentration at which still no problems arise with insolubilisation of components of the reaction system.

In the process according to the present invention, it is preferred to use lyophilised denatured protein. If, however, it is a question of a protein which only goes into solution slowly and with difficulty, then the addition takes place in dissolved form in order definitely to be able to maintain the time characteristics of the process according to the present invention.

By means of the process according to the present invention, the undesired aggregate formation which competes with the renaturation is admittedly minimised but not fully suppressed. However, the inactive aggregates formed have a substantially greater molecular weight and can, therefore, easily be removed from renatured protein by separation methods which utilise this molecular weight difference, for example molecular sieve fractionation, possibly ultrafiltration with appropriate exclusion limits, gradient centrifugation and the like. Aggregates thus separated can then, after solubilisation thereof, again be introduced into the renaturing process.

As renaturing buffer, there can be used those compositions known for this purpose. The pH value must be within the pH value range at which the protein in question has a good stability and is preferably near the pH value of maximum stability. In order to exclude the denaturing influence of impurities, for example of heavy metals, it is preferable to work in the presence of complex formers, such as ethylenediamine-tetraacetic acid (EDTA) or similar compounds. Thus, for example, in the case of lactate dehydrogenase, there can be used phosphate buffer of pH 6 to 8 which contains about 1 mM EDTA and 1 mM dithioerythritol (DTE). For lysozyme, it has proved useful to use weakly alkaline tris-HCl buffer which, besides EDTA, contains an SH group-containing substance and a small amount of the corresponding disulphide. For the renaturing of tissue-type plasminogen activator (t-PA), there can be used, for example, the reactivation buffer described in Federal Republic of Germany Patent Application No. P 3 537 708. For numerous other proteins, appropriate renaturing buffers are known or can be found on the basis of the known properties of the protein, especially with regard to pH stability, content of SH groups, heavy metal sensitivity and the like, using preliminary experiments.

It was known that, for renaturation, certain limiting values of protein concentration should not be exceeded. Now is the recognition that comparatively large amounts of denatured protein do not require larger amounts of solution volume in order to achieve larger amounts of renatured protein but that, in the same solution, by the continuous new addition or intermittent new addition of denatured protein, it is possible to obtain substantially higher concentrations of renatured protein than was held to be possible according to the prior art.

The following Examples are given for the purpose of illustrating the present invention:

EXAMPLE 1

Pulse reactivation of lysozyme (a) Preparation of the enzyme solutions

Concentration determination (A: absorption of a 1% solution at 280 nm):

native lysozyme: A=26.3
reduced lysozyme: A=23.7

Determination of the specific activity: Dissolve 2 mg. lysozyme in 1 ml. 0.066 mole/liter potassium phosphate (pH 6.2); determine concentration by UV absorption.

Test solution: suspend 2.5 mg. cell walls of

Micrococcus lysodeikticus in 10 ml. 0.066 mole/liter potassium phosphate (pH 6.2).

Test at 25° C.; 1 ml. cell wall suspension plus 0.03 ml. lysozyme solution (diluted 1:40); monitor the decrease of the turbidity at 450 nm.

Specific activity = 60,000 IU/mg.

Reduction/denaturation: Incubate 500 mg. lysozyme for 3 hours at 25° C. in 0.1 mole/liter tris/HCl (pH 8.6)+6 mole/liter guanidine hydrochloride+150 mmole/liter DTE. Adjust pH to 3 and divide up sample.

Part A

Gel filtration over Sephadex G 25 F (column volume 270 ml.) in 0.01 mole/liter hydrochloric acid. Combine peak fractions and lyophilise.

Part B

Dialyse against 3×1 liters 0.01 mole/liter hydrochloric acid at 4°C. Lyophilisation.

Both processes of desalination (part A and B) give reduced lysozyme which, with regard to reactivation properties, does not differ.

The lyophilised, reduced enzyme is stored at −40° C. under an atmosphere of nitrogen.

Reoxidation/reactivation: Dissolve 12 mg. reduced lysozyme in 1 ml. 0.01 mole/liter hydrochloric acid.

Millipore filtration

Concentration determination by UV absorption.

Reoxidation at 25° C. by dilution in 0.1 mole/liter tris/HCl (pH 8.2)+1 mmole/liter EDTA+3 mmole/liter reduced glutathione (GSH)+0.3 mmole/liter oxidized glutathione (GSSG).

(b) Determination of the critical concentration of the renaturation.

Figure 1:
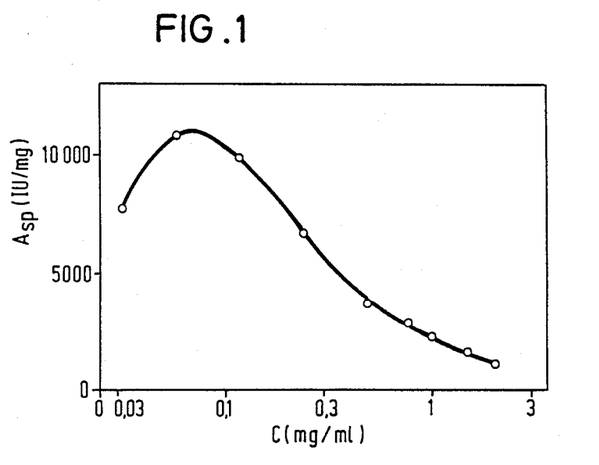

Reduction/reoxidation as described above, except for the variation of the protein concentration in the reactivation batch. FIG. 1 of the accompanying drawings shows the result, where the concentration dependence of the reactivation of reduced lysozyme after 20 hours of reoxidation at 25° C. is illustrated graphically.

(c) Time up to the formation of the folding intermediate.

Figure 2:
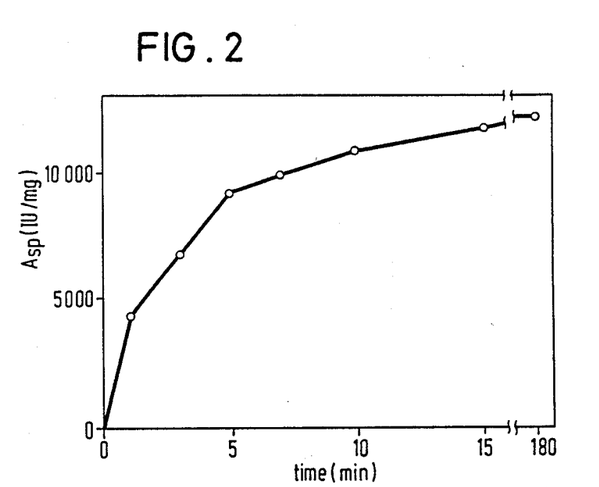

By reduction/reoxidation as described above, there is determined the kinetics of the reactivation of reduced lysozyme at a protein concentration of 0.03 mg./ml.; determined at 25° C. The result is illustrated graphically in FIG. 2 of the accompanying drawings.

(d) "Pulse reactivation" of reduced lysozyme.

1.6 or 2.4 ml. 0.125 mole/liter tris/HCl (pH 8.2) +1.25 mmole/liter EDTA+3.75 mmole/liter GSH+0.375 mmole/liter GSSG are taken.

1st Experiment

In time intervals of $t=10$ minutes, 20 μl. amounts of reduced lysozyme which is solubilized in 0.01 mole/liter hydrochloric acid are added to the above-mentioned reoxidation buffer. Concentration increase per pulse: 0.11–0.13 mg./ml. End concentration after 20 pulses: 2.15 mg./ml.

Comparative reactivation without pulse: single addition to the same end concentration. The buffer conditions correspond, after dilution, to those of the above-mentioned reoxidation buffer.

After 2 hours reactivation at 25° C.
pulse reactivation: 2200 IU/mg.
comparison without pulse: 470 IU/mg.

2nd Experiment

In time intervals of $t=10$ minutes, 30 μl amounts of reduced lysozyme which is solubilized in 0.01 mole/liter hydrochloric acid are added to the above-mentioned reoxidation buffer. Concentration increase per pulse: 0.034–0.042 mg./ml. End concentration after 20 pulses: 0.68 mg./ml.

Comparative activation: single addition to the same end concentration

After 2 hours reactivation at 25° C.:
pulse reactivation: 7660 IU/mg.
comparison without pulse: 1400 IU/mg.

3rd Experiment

In time intervals of $t=20$ minutes, 20 μl amounts of reduced lysozyme which is solubilized in 0.01 mole/liter hydrochloric acid are added to the above-mentioned reoxidation buffer. Concentration increase per pulse: 0.035–0.044 mg./ml. End concentration after 20 pulses: 0.71 mg./ml. Comparative reactivation: single addition to the same end concentration After 24 hours reactivation at 25° C.:
pulse reactivation 10100 IU/mg.
comparison without pulse: 1400 IU/mg.

From these results, it follows that: the reactivation yields in the case of protein concentrations of $>0.1$ mg./ml. decrease continuously; at 25° C., the reactivation under the given reoxidation conditions is almost complete after 15 minutes (FIG. 2); by "pulse reactivation" according to the present invention, in comparison with the reactivation without pulse, there can be achieved a 5 to 7 fold higher yield.

EXAMPLE 2

"Pulse reactivation" of LDH-$M_4$ (a) Preparation of the enzyme solution:

LDH-$M_4$ (from pig muscle) suspension in ammonium sulphate (producer: Boehringer Mannheim GmbH, Order No. 107077) is centrifuged and the pellet is dissolved in one sixth of the original volume of 0.1 mole/liter potassium phosphate (pH 7.6)+1 mmole/liter EDTA+1 mmole/liter DTE and dialysed against $2\times 1$ liter of the same buffer at 4° C. Concentration determination via $A=14$ (A=absorption of a 1% solution at 280 nm). The activity test at 25° C. according to R. Hermann, R. Jaenicke and R. Rudolph (Biochemistry, 20, 5195–5201/1981) gives a specific activity of 300 IU/mg.

Denaturation/reactivation: Denaturation: 1:5 dilution with 0.1 mole/liter phosphoric acid, 6 minutes incubation at 0° C. Reactivation: 1:3 dilution with 0.1 mole/liter potassium phosphate (pH 12.65)+1 mmole/liter EDTA+1 mmole/liter DTE at 20° C.; after mixing, the pH of the solution is 7.6.

(b) Determination of the critical concentration of the renaturation.

Denaturation./reactivation take place as described above with variation of the protein concentration in the denaturing batch.

Figure 3:
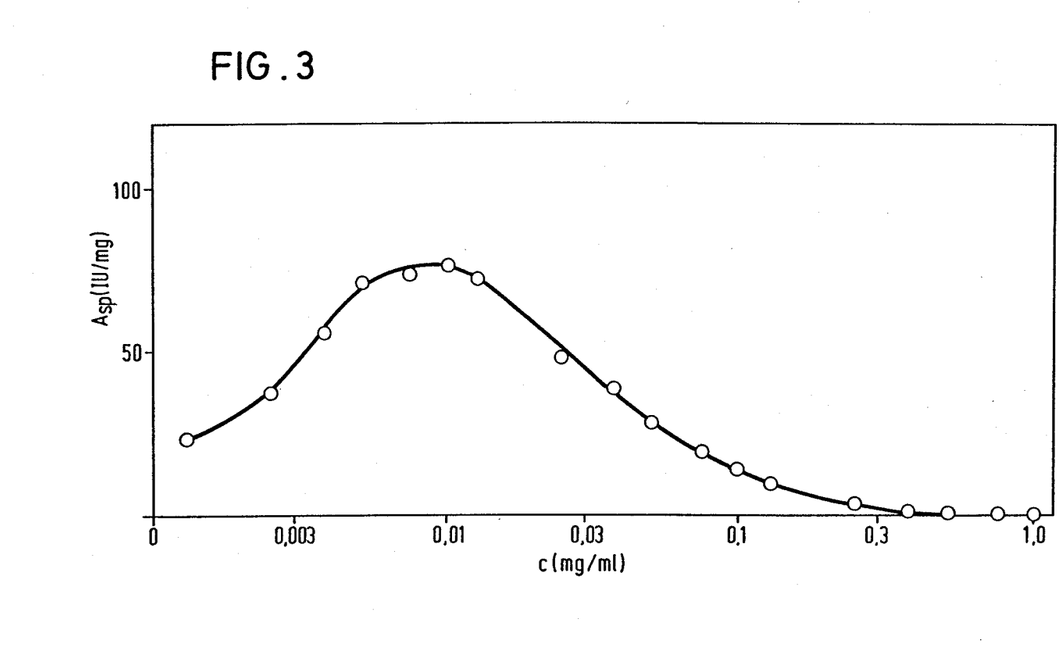

FIG. 3 of the accompanying drawings shows the concentration dependency of the reactivation of LDH-$M_4$ obtained after acid denaturation, the activity after 20 hours reactivation at 25° C. being plotted against the concentration.

(c) Determination of the time up to the formation of the folding intermediate.

Figure 4:
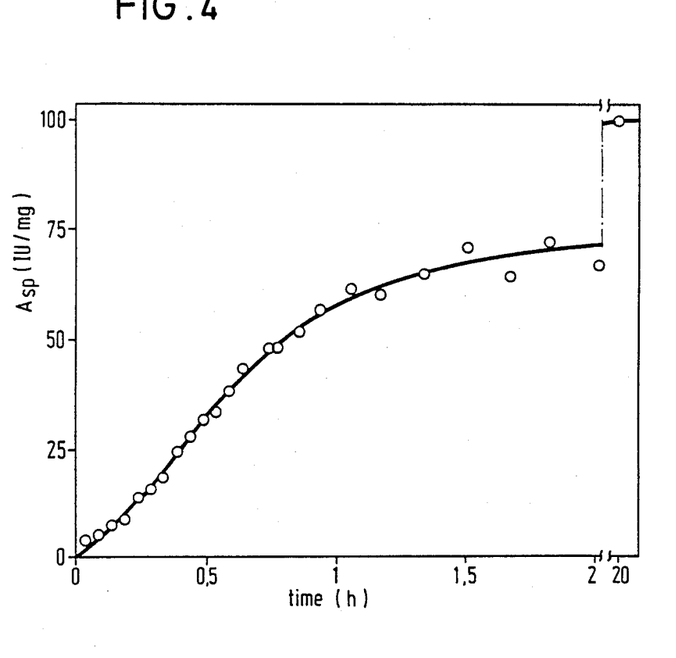

By denaturation/renaturation as above, there is determined the kinetics of the reactivation of acid-denatured LDH-$M_4$ at a protein concentration of 0.01 mg./ml. determined at 25° C. FIG. 4 of the accompanying drawings shows the result.

(d) Continuous reactivation of acid-denatured LDH-$M_4$.

Into a closed reactor, there are continuously fed in acid-denaturised LDH-$M_4$ and reactivation buffer.

Figure 5:
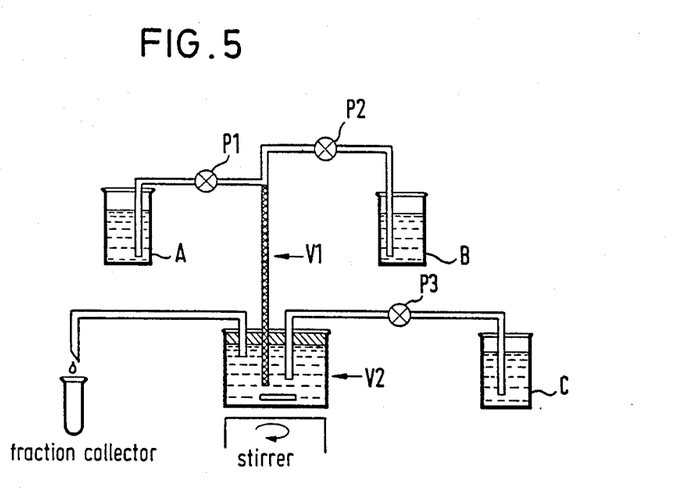

The reactivation reactor used is schematically illustrated in FIG. 5 of the accompanying drawings.

From storage vessels A and B, there is continuously fed in the solution of the enzyme and denaturing solution via pumps $P_1$ and $P_2$ and denatured in a mixing section V1. The denatured enzyme solution is continuously fed into a renaturation reactor V2. At the same time, renaturation buffer from storage vessel C is also continuously fed in via pump $P_3$ into the reactor V2. Renatured solution is continuously withdrawn and collected in a fraction collector 6. The composition of the solutions and the conditions present in the reactor are as follows:

A: 7.43 mg./ml. LDH-$M_4$ in 0.1 mole/liter potassium phosphate (pH 7.6)+1 mmole/liter DTE+1 mmole/liter EDTA at 0° C.

B: denaturation buffer: 0.1 mole/liter phosphoric acid at 0° C.

C: renaturation buffer: 0.1 mole/liter potassium phosphate (pH 12.6)+1 mmole/liter DTE+1 mmole/liter EDTA at 25° C. (pH after mixing with B: 7.6)

V1: denaturation volume $V_1 = 0.25$ ml. Gives a denaturation period of 3 minutes at 0° C.

V2: renaturation volume $V_2 = 58$ ml. at 25° C.

Pump velocity: $P_1 = 1$ ml./hour
$P_2 = 4$ ml./hour
$P_3 = 10$ ml./hour

With the given reactor size/pump rate, the average residence time of a molecule in the reactor is 2.9 hours.

In the case of the run, 2.5 ml. samples are collected and the end reactivation determined after 24 hours at 25° C.

Figure 6:
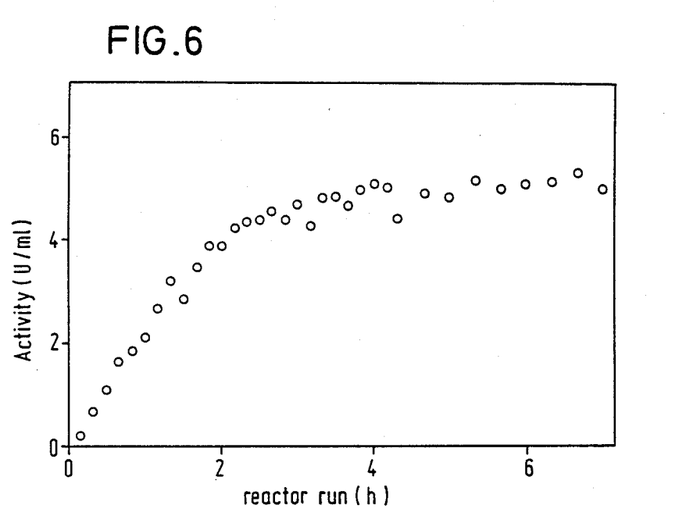

FIG. 6 of the accompanying drawings shows the activity increase in the case of charging the reactor.

After about 4 hours, a constant reactivation yield is achieved.

end concentration of the reactivation: 0.5 mg./ml.
yield: continuous reactivation: 10.2 IU/mg.
comparison without continuous reactivation: 1.9 IU/mg.

The above results show that, according to the present invention, there is achieved an approximately 5.4 times higher yield than in the case of a direct reactivation with the same end concentration.

EXAMPLE 3

Pulse reactivation of rec-t-PA (a) Preparation of the "refractile bodies" (RB).

RB preparation by cell digestion and diverse centrifuging/washing steps takes place analogously to the process of European Patent Specification No. 0114506, Example 7. t-PA is contaminated in the RB's with foreign protein and it is inactive and insoluble.

Solubilisation by reduction/denaturation: RB's from 2.5 g. of cells are incubated for 3 hours at 25° C. in 10 ml. 0.1 mole/liter tris/HCl (pH 8.6)+6 mole/liter guanidine hydrochloride+1 mmole/liter EDTA+150 mmole/liter, DTE.

Total protein in the RB's after reduction: 41.5 mg.

The pH is adjusted to 3 with concentrated hydrochloric acid and gel filtered over Sephadex G 25 F (column volume=270 ml.) in 0.01 mole/liter hydrochloric acid.

(b) Determination of the concentration dependency of the reactivation.

The acidic fraction of the reduced protein with maximum recovery of activity (c=0.83 mg./ml.) is reoxidized by 1:3 to 1:500 dilution in 0.1 mole/liter tris/HCl (pH 10.4)+1 mmole/liter EDTA+0.5 mole/liter L-arginine+1 mg./ml. bovine serum albumin (BSA)+1 mmole/liter reduced glutathion (GSH)+0.2 mmole/liter glutathion disulfide (GSSG).

Figure 7:
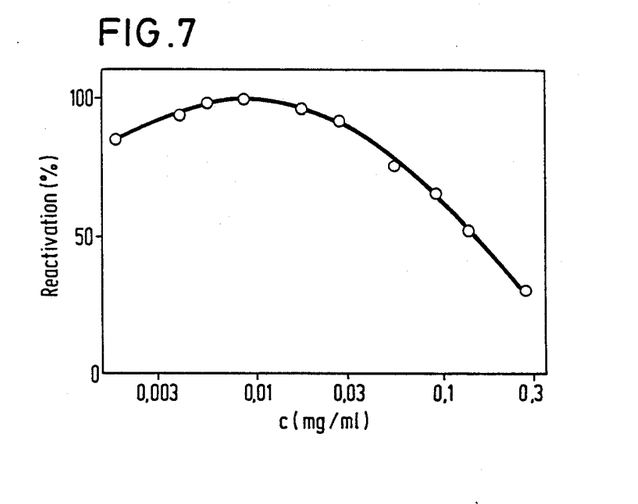

The reoxidation conditions in the case of various dilutions are constantly adjusted. After 25 to 27 hours reoxidation at 25°C., the activity is determined. Before the activity measurement, the protein concentration is adjusted with reoxidation buffer to the same end concentration. The results obtained are shown in the following Table 1 and in FIG. 7 of the accompanying drawings.

TABLE 1

| Concentration dependency of the reactivation of rec-t-PA | | |
|---|---|---|
| protein concentration[1] (μg./ml.) | yield[2] | stimulation (factor) |
| 277 | 31.3 | 16.8 |
| 138 | 52.4 | 17.0 |
| 92.2 | 64.9 | 18.5 |
| 55.3 | 74.9 | 21.5 |
| 27.7 | 91.5 | 17.5 |
| 17.3 | 95.6 | 25.3 |
| 8.68 | 100.0 | 20.5 |
| 5.53 | 97.8 | 19.8 |
| 3.95 | 94.4 | 20.6 |
| 1.84 | 85.3 | 16.7 |

[1] protein concentration in the case of reactivation (total protein)
[2] referred to maximum reactivation value (c) Determination of the kinetics of the reactivation.

Reduction/reoxidation are carried out as above.

Because of the impurity of the material, the time up to the formation of the folding intermediate cannot be measured directly but rather indirectly via the kinetics of the reactivation and variation of the pulse rate to about 40 to 60 minutes.

Figure 8:
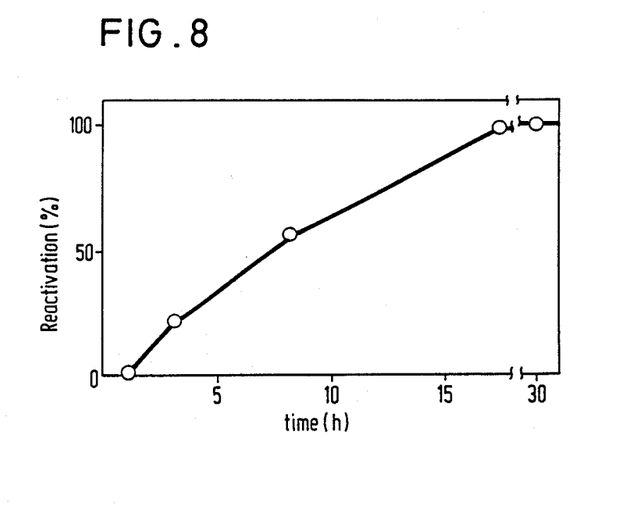

FIG. 8 of the accompanying drawings shows the kinetics of the reactivation of rec-t-PA at a total protein concentration of 15 μg./ml. at 20° C. Reactivation referred to final yield after 30 hours.

(d) "Pulse reactivation" of rec-t-PA.

In time intervals between 2 minutes and 45 minutes, 10 μl. amounts of reduced rec-t-PA in 0.01 mole/liter hydrochloric acid are introduced into 300 μl. reactivation buffer at 25° C.

Reactivation buffer before pulse reactivation: 0.15 mole/liter tris/HCl (pH 10.5)+1.5 mmole/liter EDTA+0.5 mole/liter L-arginine+0.3 mmole/liter GSSG+1.5 mmole/liter GSH.

Reactivation buffer after the addition of the reduced protein: 0.1 mole/liter tris/HCl (pH 10.4)+1 mmole/liter EDTA+0.33 mole/liter L-arginine+0.2 mmole/liter GSSG+1 mmole/liter GSH.

Concentration increase per pulse: 18 to 27 μg./ml.

End concentration after 15 pulses: 227 μg./ml.

Activity measurement takes place after 24 hours reoxidation at 20° C. The following Table 2 shows the results obtained:

TABLE 2

| Pulse reactivation of rec-t-PA | | |
|---|---|---|
| pulse rate (min) | yield[1] (%) | stimulation (factor) |
| 2 | 31.3 | 7.1 |
| 10 | 38.6 | 8.1 |
| 20 | 39.5 | 9.0 |
| 30 | 44.8 | 8.2 |
| 45 | 45.8 | 7.8 |

Commentary

In the case of the starting material used, the reactivation yield, referred to the amount of protein used, decreases at concentrations of >20 μg./ml. (see FIG. 7 of the accompanying drawings). The stimulation by CNBr-FSP proves, in the range of error, to be independent of the reactivation concentration (Table 1).

At 20° C., the half life value of the reactivation is, under the given conditions, 7±2 hours.

The reactivation yield increases with increasing residence time between the reactivation pulses (Table 2).

We claim:

1. Process for renaturation of a denatured protein comprising adding a solution of protein to be renatured and a buffer to a renaturation buffer, to form a folding intermediate of said protein to be renatured, and adding further protein to be renatured to said renaturation buffer in an amount necessary to achieve a critical concentration at which concentration said folded intermediate passes over into a renatured protein.

2. Process according to claim 1, wherein after formation of the folded intermediate an amount of denatured protein necessary to regain the critical concentration of said denatured protein is added to said renaturation buffer.

3. Process according to claim 1, comprising continuously introducing into a reactor an amount of denatured protein to maintain the critical concentration and adjusting the corresponding amount of renaturation buffer and residence time of a mixture of said renaturation buffer and said denatured protein in the reaction to a time necessary for formation of said folding intermediate.

4. Process according to claim 3, wherein said denatured protein remains in the reactor until a desired concentration of renatured protein is reached and continuously removing the solution thus obtained and replaced by a solution of denatured protein.

5. Process according to claim 1, comprising separating inactive protein aggregate on the basis of its higher molecular weight as compared to renatured protein dissolving said aggregate to form individual protein molecules and reintroducing said protein into said renaturation buffer.

6. Process according to claim 1, wherein said denatured protein is introduced in lyophilized form.

* * * * *